US011877913B2

(12) United States Patent
Bunnelle et al.

(10) Patent No.: US 11,877,913 B2
(45) Date of Patent: *Jan. 23, 2024

(54) ABSORBENT ARTICLE WITH TACKIFIER-FREE ADHESIVE

(71) Applicant: The Procter & Gamble Company, Cincinnati, OH (US)

(72) Inventors: William L. Bunnelle, Ham Lake, MN (US); Robert Haines Turner, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/893,222

(22) Filed: Aug. 23, 2022

(65) Prior Publication Data

US 2022/0409438 A1 Dec. 29, 2022

Related U.S. Application Data

(63) Continuation of application No. 16/839,433, filed on Apr. 3, 2020, now Pat. No. 11,497,654, which is a
(Continued)

(51) Int. Cl.
*A61F 13/15* (2006.01)
*A61L 15/42* (2006.01)
(Continued)

(52) U.S. Cl.
CPC .. *A61F 13/15203* (2013.01); *A61F 13/15699* (2013.01); *A61L 15/24* (2013.01);
(Continued)

(58) Field of Classification Search
CPC ........ A61L 15/585; A61L 15/24; A61L 15/42; A61L 2300/802; A61F 13/15203;
(Continued)

(56) References Cited

U.S. PATENT DOCUMENTS 3,338,992 A 8/1967 Allison
3,341,394 A 9/1967 Allison
(Continued)

FOREIGN PATENT DOCUMENTS

EP 1171073 B1 6/2005
JP 2008237252 A 10/2008
(Continued)

OTHER PUBLICATIONS

PCT Search Report and Written Opinion for PCT/US2014/069985 dated Mar. 18, 2015, 10 pages.
(Continued)

*Primary Examiner* — Michele Kidwell
(74) *Attorney, Agent, or Firm* — Amanda Herman Berghauer; Daniel Albrecht

(57) ABSTRACT

Disposable absorbent articles assembled from a collection of components using an adhesive composition is disclosed. The adhesive composition comprises at least 90 wt. % of a copolymer, wherein the copolymer comprises from about 30 mole % to about 70 mole % of propene monomer units and from about 30 mole % to about 75 mole % of 1-butene monomer units. The adhesive composition is free of a heterophase copolymer.

20 Claims, 1 Drawing Sheet

Related U.S. Application Data continuation of application No. 14/302,745, filed on Jun. 12, 2014, now Pat. No. 10,639,210.

(60) Provisional application No. 61/918,434, filed on Dec. 19, 2013.

(51) Int. Cl.

| | | |
|---|---|---|
| C08L 23/22 | (2006.01) | |
| C09J 5/06 | (2006.01) | |
| C09J 123/22 | (2006.01) | |
| A61L 15/24 | (2006.01) | |
| A61L 15/58 | (2006.01) | |
| B32B 7/12 | (2006.01) | |
| B32B 23/00 | (2006.01) | |
| C09J 123/20 | (2006.01) | |

(52) U.S. Cl.
CPC ............ *A61L 15/42* (2013.01); *A61L 15/585* (2013.01); *B32B 7/12* (2013.01); *B32B 23/00* (2013.01); *C08L 23/22* (2013.01); *C09J 5/06* (2013.01); *C09J 123/20* (2013.01); *C09J 123/22* (2013.01); *A61F 2013/15569* (2013.01); *A61L 2300/802* (2013.01); *B32B 2250/02* (2013.01); *B32B 2555/02* (2013.01); *C08L 2205/025* (2013.01); *C08L 2207/324* (2013.01); *C09J 2301/304* (2020.08); *Y10T 428/3188* (2015.04); *Y10T 428/31938* (2015.04)

(58) Field of Classification Search
CPC ..... A61F 13/15699; A61F 2013/15569; B32B 7/12; B32B 2250/02; B32B 23/00; B32B 2555/02; C08L 2205/025; C08L 2207/324; C08L 23/20; C08L 23/22; C09J 123/20; C09J 123/22; C09J 2301/304; C09J 5/06; Y10T 428/31938; Y10T 428/3188
See application file for complete search history.

(56) References Cited

U.S. PATENT DOCUMENTS

| | | |
|---|---|---|
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,848,594 A | 11/1974 | Buell |
| 3,849,241 A | 11/1974 | Butin et al. |
| 3,860,003 A | 1/1975 | Buell |
| 4,046,945 A | 9/1977 | Baxmann et al. |
| 4,340,563 A | 7/1982 | Appel et al. |
| 4,610,678 A | 9/1986 | Weisman |
| 4,662,875 A | 5/1987 | Hirotsu |
| 4,673,402 A | 6/1987 | Weisman |
| 4,699,622 A | 10/1987 | Toussant |
| 4,761,450 A | 8/1988 | Lakshmanan et al. |
| 4,808,178 A | 2/1989 | Aziz |
| 4,834,735 A | 5/1989 | Alemany |
| 4,846,815 A | 7/1989 | Scripps |
| 4,857,594 A | 8/1989 | Lakshmanan et al. |
| 4,888,231 A | 12/1989 | Angstadt |
| 4,892,536 A | 1/1990 | Desmarais |
| 4,894,060 A | 1/1990 | Nestegard |
| 4,909,803 A | 3/1990 | Aziz |
| 4,940,464 A | 7/1990 | Van |
| 4,946,527 A | 8/1990 | Battrell |
| 4,963,140 A | 10/1990 | Robertson |
| 4,990,147 A | 2/1991 | Freeland |
| 5,037,416 A | 8/1991 | Allen |
| 5,092,861 A | 3/1992 | Nomura |
| 5,137,537 A | 8/1992 | Herron |
| 5,147,345 A | 9/1992 | Lavon |
| 5,151,092 A | 9/1992 | Buell |
| 5,213,881 A | 5/1993 | Timmons et al. |
| 5,217,812 A | 6/1993 | Lee |
| 5,221,274 A | 6/1993 | Buell |
| 5,242,436 A | 9/1993 | Weil |
| 5,246,433 A | 9/1993 | Hasse |
| 5,260,345 A | 11/1993 | Desmarais |
| 5,269,775 A | 12/1993 | Freeland |
| 5,342,338 A | 8/1994 | Roe |
| 5,387,207 A | 2/1995 | Dyer |
| 5,391,434 A | 2/1995 | Krutzel |
| 5,397,316 A | 3/1995 | Young |
| 5,499,978 A | 3/1996 | Buell |
| 5,507,736 A | 4/1996 | Clear |
| 5,554,145 A | 9/1996 | Roe |
| 5,569,234 A | 10/1996 | Buell |
| 5,571,096 A | 11/1996 | Dobrin |
| 5,580,411 A | 12/1996 | Nease |
| 5,591,152 A | 1/1997 | Buell |
| 5,607,760 A | 3/1997 | Roe |
| 5,609,587 A | 3/1997 | Roe |
| 5,625,222 A | 4/1997 | Yoneda |
| 5,635,191 A | 6/1997 | Roe |
| 5,637,665 A | 6/1997 | Sustic et al. |
| 5,643,588 A | 7/1997 | Roe |
| 5,681,913 A | 10/1997 | Sustic et al. |
| 5,685,758 A | 11/1997 | Paul et al. |
| 5,714,554 A | 2/1998 | Sustic et al. |
| 5,723,546 A | 3/1998 | Sustic |
| 5,804,519 A | 9/1998 | Riswick et al. |
| 5,865,823 A | 2/1999 | Curro |
| 5,897,545 A | 4/1999 | Kline |
| 5,957,908 A | 9/1999 | Kline |
| 5,998,547 A | 12/1999 | Hohner |
| 6,004,306 A | 12/1999 | Robles |
| 6,107,537 A | 8/2000 | Elder |
| 6,120,487 A | 9/2000 | Ashton |
| 6,120,489 A | 9/2000 | Johnson |
| 6,140,551 A | 10/2000 | Niemeyer et al. |
| 6,143,818 A | 11/2000 | Wang et al. |
| 6,218,457 B1 | 4/2001 | Fralich et al. |
| 6,281,288 B1 | 8/2001 | Bickert et al. |
| 6,432,098 B1 | 8/2002 | Kline |
| 6,486,246 B1 | 11/2002 | Vion |
| 6,489,400 B2 | 12/2002 | Khandpur et al. |
| 6,582,762 B2 | 6/2003 | Faissat et al. |
| 6,677,396 B2 | 1/2004 | Tsui et al. |
| 6,747,114 B2 | 6/2004 | Karandinos et al. |
| 6,767,424 B1 | 7/2004 | Butterbach et al. |
| 6,887,941 B2 | 5/2005 | Zhou |
| 6,992,131 B2 | 1/2006 | Faissat et al. |
| 7,067,585 B2 | 6/2006 | Wang et al. |
| 7,163,741 B2 | 1/2007 | Khandpur et al. |
| 7,199,180 B1 | 4/2007 | Simmons et al. |
| 7,262,251 B2 | 8/2007 | Kanderski et al. |
| 7,270,889 B2 | 9/2007 | Campbell et al. |
| 7,348,376 B2 | 3/2008 | Gelles |
| 7,517,579 B2 | 4/2009 | Campbell et al. |
| 7,521,507 B2 | 4/2009 | Lewtas et al. |
| 7,524,910 B2 | 4/2009 | Jiang et al. |
| 7,626,073 B2 | 12/2009 | Catalan |
| 7,927,703 B2 | 4/2011 | Xia et al. |
| 8,017,827 B2 | 9/2011 | Hundorf et al. |
| 8,084,527 B2 | 12/2011 | Paschkowski et al. |
| 8,193,289 B2 | 6/2012 | Abhari et al. |
| 8,226,625 B2 | 7/2012 | Turner |
| 8,226,626 B2 | 7/2012 | Turner et al. |
| 8,231,595 B2 | 7/2012 | Turner et al. |
| 8,388,594 B2 | 3/2013 | Turner |
| 8,496,637 B2 | 7/2013 | Hundorf et al. |
| 9,241,843 B2 | 1/2016 | Bunnelle et al. |
| 9,456,932 B2 | 10/2016 | Digiacomantonio et al. |
| 9,555,152 B2 | 1/2017 | Bunnelle et al. |
| 9,943,623 B2 | 4/2018 | Bunnelle |
| 10,300,164 B2 | 5/2019 | Bunnelle et al. |
| 10,357,407 B2 | 7/2019 | Bunnelle |
| 10,639,210 B2 | 5/2020 | Bunnelle et al. |

(56) References Cited

U.S. PATENT DOCUMENTS

| | | | |
|---|---|---|---|
| 10,729,803 B2 | 8/2020 | Bunnelle et al. | |
| 11,497,654 B2 * | 11/2022 | Bunnelle | A61L 15/24 |
| 2004/0038058 A1 | 2/2004 | Zhou | |
| 2004/0204529 A1 | 10/2004 | Gipson | |
| 2007/0042193 A1 | 2/2007 | Wang | |
| 2007/0055211 A1 | 3/2007 | Shunketsu et al. | |
| 2007/0117894 A1 | 5/2007 | Bach et al. | |
| 2007/0117907 A1 | 5/2007 | Bach et al. | |
| 2007/0142801 A1 | 6/2007 | Zhou et al. | |
| 2007/0187032 A1 | 8/2007 | Wang | |
| 2008/0312617 A1 | 12/2008 | Hundorf | |
| 2008/0312618 A1 | 12/2008 | Hundorf et al. | |
| 2008/0319116 A1 | 12/2008 | Fredrickson et al. | |
| 2009/0326494 A1 | 12/2009 | Uchida et al. | |
| 2010/0160497 A1 | 6/2010 | Karjala et al. | |
| 2010/0305531 A1 | 12/2010 | Bach et al. | |
| 2011/0021102 A1 | 1/2011 | Inoue et al. | |
| 2011/0021103 A1 | 1/2011 | Alper et al. | |
| 2011/0082256 A1 | 4/2011 | Batra et al. | |
| 2011/0104508 A1 | 5/2011 | Wang et al. | |
| 2011/0167074 A1 | 7/2011 | Heinze et al. | |
| 2012/0149827 A1 | 6/2012 | Hu et al. | |
| 2012/0165455 A1 | 6/2012 | Vitrano et al. | |
| 2012/0171466 A1 | 7/2012 | Urbach et al. | |
| 2012/0178333 A1 | 7/2012 | Fowler et al. | |
| 2012/0328805 A1 | 12/2012 | Davis | |
| 2012/0329353 A1 | 12/2012 | Davis et al. | |
| 2013/0158176 A1 | 6/2013 | Hu et al. | |
| 2014/0079919 A1 | 3/2014 | Bunnelle | |
| 2014/0296811 A1 | 10/2014 | Bunnelle | |
| 2015/0173958 A1 | 6/2015 | Bunnelle | |
| 2015/0174281 A1 | 6/2015 | Bunnelle | |
| 2015/0174286 A1 | 6/2015 | Bunnelle | |
| 2018/0078425 A1 | 3/2018 | Bunnelle | |
| 2020/0222251 A1 | 7/2020 | Turner | |
| 2020/0222579 A1 | 7/2020 | Turner | |
| 2020/0229984 A1 | 7/2020 | Bunnelle et al. | |
| 2020/0268568 A1 | 8/2020 | Turner | |
| 2020/0316246 A1 | 10/2020 | Bunnelle et al. | |

FOREIGN PATENT DOCUMENTS

| | | |
|---|---|---|
| RU | 2185857 C2 | 7/2002 |
| RU | 2407498 C1 | 12/2010 |
| WO | 9516746 A1 | 6/1995 |
| WO | 9849249 A1 | 11/1998 |
| WO | 02053669 A2 | 7/2002 |
| WO | 2007026334 A2 | 3/2007 |
| WO | 2012027450 A2 | 3/2012 |
| WO | 2013019507 A2 | 2/2013 |

OTHER PUBLICATIONS

PCT Search Report and Written Opinion for PCT/US2014/069990 dated Mar. 19, 2015, 10 pages.
All Office Actions; U.S. Appl. No. 14/302,736, filed Jun. 12, 2014.
All Office Actions; U.S. Appl. No. 14/302,745, filed Jun. 12, 2014.
All Office Actions; U.S. Appl. No. 15/826,928, filed Nov. 30, 2017.
All Office Actions; U.S. Appl. No. 16/839,433, filed Apr. 3, 2020.
Indopol Polybutene Product Data, INEOS Oligomers, Sep. 17, 2012, 02 Pages.
Linxar 127 Polymer Data Sheet, ExxonMobil Chemical, Nov. 2010, 1 page.
REXtac LLC, Advance Technology, 1990, 2 pages.
Roduct datasheets for Vistamaxx, ExxonMobil Chemical, Sep. 17, 2012, 1 page.
Vistamaxx 2330 Propylene-based Elastomer, ExxonMobil Chemical, Jan. 26, 2011, 2 pages.

* cited by examiner

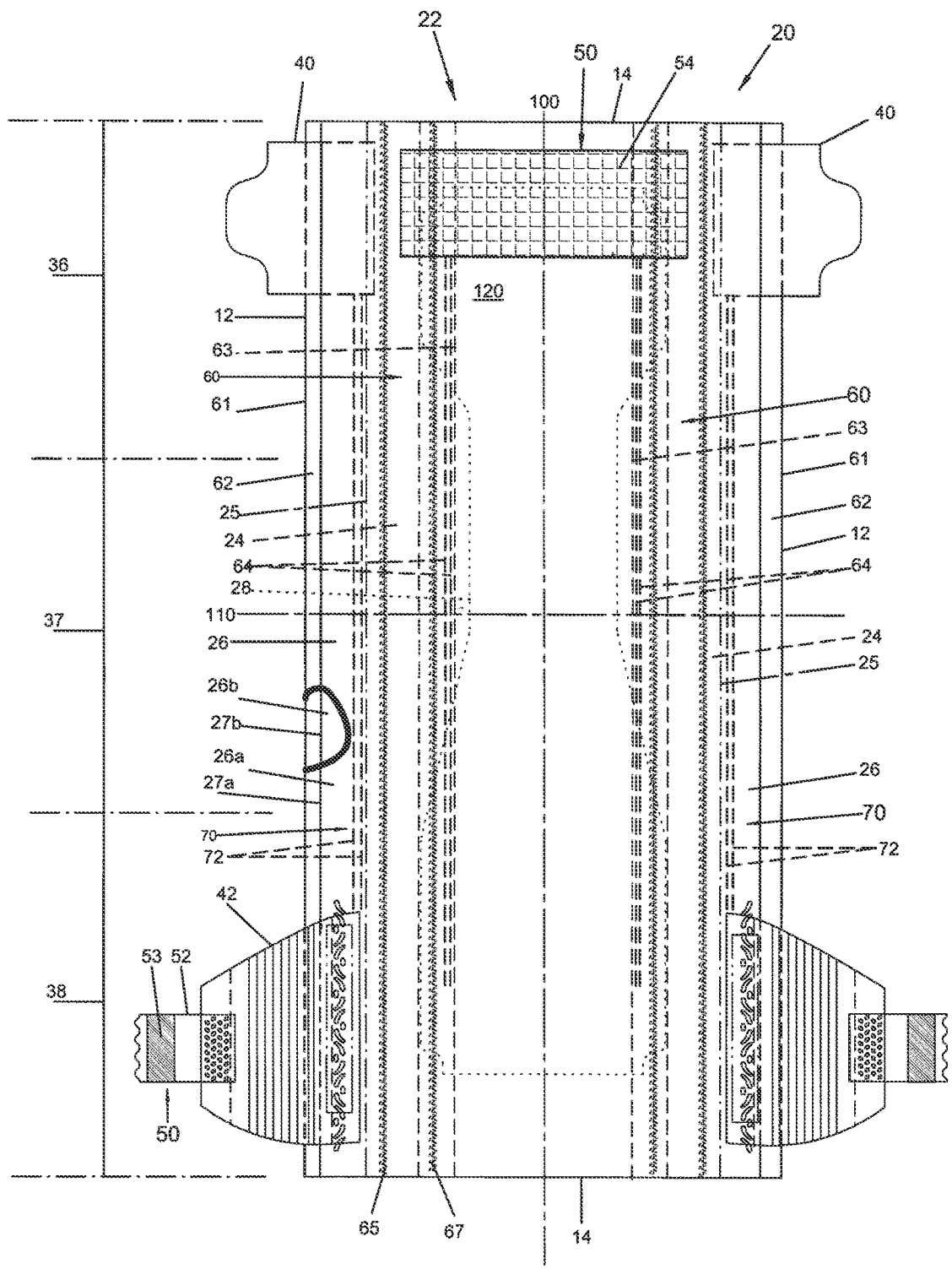

ABSORBENT ARTICLE WITH TACKIFIER-FREE ADHESIVE

CROSS-REFERENCE TO RELATED APPLICATIONS

This application claims priority under 35 U.S.C. § 120 to, and is a continuation of U.S. patent application Ser. No. 16/839,433, filed on Apr. 3, 2020, which is a continuation of, U.S. patent application Ser. No. 14/302,745, filed on Jun. 12, 2014; which claims the benefit under 35 U.S.C. 119(e) of U.S. Provisional Application Ser. No. 61/918,434, filed Dec. 19, 2013, each of which are herein incorporated by reference in their entirety.

FIELD

This invention relates to the adhesive material, typically a hot melt adhesive, that is used to assemble components into an absorbent article such as a diaper (i.e., the construction adhesive). In particular, this invention relates to such absorbent articles assembled using a construction adhesive that is substantially free of a tackifier.

BACKGROUND

Users, for example caregivers, rely on disposable absorbent articles to make their lives easier. Disposable absorbent articles, such as adult incontinence articles, diapers, and training pants are generally manufactured by combining several components. These components typically include a liquid-permeable topsheet, a liquid-impermeable backsheet attached to the topsheet, and an absorbent core located between the topsheet and the backsheet. When the disposable article is worn, the liquid-permeable topsheet is positioned next to the body of the wearer. The topsheet allows passage of bodily fluids into the absorbent core. The liquid-impermeable backsheet helps prevent leakage of fluids held in the absorbent core. The absorbent core generally is designed to have desirable physical properties, e.g. a high absorbent capacity and high absorption rate, so that bodily fluids can be transported from the skin of the wearer into the disposable absorbent article.

Frequently one or more components of a disposable absorbent article are adhesively bonded together. For example, adhesives have been used to bond individual layers of the absorbent article, such as the topsheet and backsheet together. Adhesives have also been used to bond discrete components, such as fasteners and leg elastics or cuffs, to the article. The adhesive is often called a construction adhesive because it is used to help construct the absorbent article from individual components.

In many instances, a hot-melt adhesive is used as a construction adhesive. Common hot-melt adhesives are made by combining polymer and additive components in a substantially uniform thermoplastic blend. Typical additives may include tackifiers, plasticizers, and/or waxes, for example.

While such formulations generally work, they can be costly and their performance properties can be improved. For example, tackifiers, which can comprise up to 65% of an adhesive formula, can be expensive and difficult to source. Therefore, there is a continuing need for improved construction adhesives that offer better performance and lower cost.

SUMMARY

The present invention relates to disposable absorbent articles assembled from a collection of components using an adhesive consisting essentially of an amorphous polyolefin composition comprising more than 40% 1-butene and a second amorphous polymer comprising at least one butene monomer, the polymer having a molecular weight ($MW_n$) of at least 1000 wherein the polymer is compatible with the polyolefin.

BRIEF DESCRIPTION OF THE DRAWINGS

FIG. 1 is a plan view of an exemplary absorbent article in a flat, uncontracted state.

DETAILED DESCRIPTION

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, adult incontinence briefs and undergarments, diaper holders and liners, feminine hygiene garments such as panty liners, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal".

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable."

"Extendibility" and "extensible" mean that the width or length of the component in a relaxed state can be extended or increased.

"Elastic," "elastomer," and "elastomeric" refer to a material which generally is able to extend to a strain of at least 50% without breaking or rupturing, and is able to recover substantially to its original dimensions after the deforming force has been removed.

"Elastomeric material" is a material exhibiting elastic properties. Elastomeric materials may include elastomeric films, scrims, nonwovens, and other sheet-like structures.

"Outboard" and "inboard" refer respectively to the location of an element disposed relatively far from or near to the longitudinal centerline of the diaper with respect to a second element. For example, if element A is outboard of element B, then element A is farther from the longitudinal centerline than is element B.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Nonwoven" fabric or web means a web having a structure of individual fibers or threads that are interlaid, but not in a regular or identifiable manner as in a knitted fabric. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note: to convert from osy to gsm, multiply osy by 33.91.)

"Substrate" is used herein to describe a material that is primarily two-dimensional (i.e., in an XY plane) and whose thickness (in a Z direction) is relatively small (i.e. 1/10 or less) in comparison to its length (in an X direction) and width (in a Y direction). Non-limiting examples of substrates include a web, layer or layers of fibrous materials, nonwovens, and films and foils, such as polymeric films or metallic foils, for example. These materials may be used alone or may comprise two or more layers laminated together. As such, a web may be a substrate or may be a laminate of two or more substrates.

"Spunbonded fibers", or "spunbond fibers", means small-diameter fibers that are typically formed by extruding molten thermoplastic material as filaments from a plurality of fine capillaries of a spinneret having a circular or other configuration, with the diameter of the extruded filaments then being rapidly reduced as by, for example, in U.S. Pat. Nos. 4,340,563, 3,692,618, 3,802,817, 3,338,992, 3,341,394, 3,502,763, 3,502,538, and 3,542,615. Spunbond fibers are quenched and generally not tacky when they are deposited onto a collecting surface. Spunbond fibers are generally continuous and often have average diameters larger than about 7 microns, and more particularly between about 10 and 30 microns. A spunbond material, layer, or substrate comprises spunbonded (or spunbond) fibers.

"Meltblown fibers" means fibers formed by extruding a molten material, typically thermoplastic in nature, through a plurality of fine, usually circular, die capillaries as molten threads or filaments into converging high-velocity heated gas (e.g., air) streams that attenuate the filaments of molten material to reduce their diameter, which may be to microfiber diameter. Thereafter, the meltblown fibers are carried by the high-velocity gas stream and are deposited on a collecting surface to form a web of randomly dispersed meltblown fibers. Such a process is disclosed for example, in U.S. Pat. No. 3,849,241. Meltblown fibers are microfibers which may be continuous or discontinuous, are generally smaller than 10 microns in diameter, and are generally self-bonding when deposited onto a collecting surface "Microfibers" means small-diameter fibers having an average diameter not greater than about 100 microns, for example, having a diameter of from about 0.5 microns to about 50 microns, more specifically microfibers may also have an average diameter of from about 1 micron to about 20 microns. Microfibers having an average diameter of about 3 microns or less are commonly referred to as ultra-fine microfibers. A description of an exemplary process of making ultra-fine microfibers may be found in, for example, U.S. Pat. No. 5,213,881.

"Homopolymer" means a polymer resulting from the polymerization of a single monomer, i.e., a polymer consisting essentially of a single type of repeating unit.

"Copolymer(s)" refers to polymer(s) formed by the polymerization of at least two different monomers. For example, the term "copolymer" includes the copolymerization reaction product of a monomer such as propene or 2-butene, preferably 1-butene and an a-olefin, such as for example, ethylene, 1-hexene or 1-octene.

"Propene copolymer" or "propylene copolymer" means a copolymer of greater than 40 or 50 wt. % or more propene and at least one monomer selected from the group including ethylene and a $C_4$ to $C_{20}$ α-olefin.

"Butene copolymer" means a polymer of n-butene (1-butene) or 2-butene and at least one monomer selected from the group of $C_{2-3}$ and $C_{5-20}$ alpha olefins. Butene copolymers typically comprise a minimum amount at least about 40 or about 50 wt.% or more of a butene monomer such as 1-butene.

"Heterophase" polymer means a polymer having an amorphous character and at least some substantial crystalline content (at least 5 wt. %, 10 wt. %, 20 wt. %, 40 wt. % or 50 wt. % crystalline content) that can provide cohesive strength in the cooled adhesive mass. The crystalline content can be in the form of stereoregular blocks or sequences.

"Amorphous" means the substantial absence of crystallinity, (i.e.) less than 5% and less than 1%.

"Sequence or block" means a polymer portion of repeating monomer that is similar in composition, crystallinity or other aspect.

"Open time" means the amount of time elapsed between application of a molten hot melt adhesive composition to a first substrate, and the time when useful tackiness or wetting out of the adhesive on a substrate effectively ceases due to solidification of the adhesive composition. Open time is also referred to as "working time."

"Substantially" means generally the same or uniform but allowing for or having minor fluctuations from a defined property, definition, etc. For example, small measureable or immeasurable fluctuations in a measured property described herein, such as viscosity, melting point, etc. may result from human error or methodology precision. Other fluctuations are caused by inherent variations in the manufacturing process, thermal history of a formulation, and the like. The adhesive compositions of the, nonetheless, would be said to be substantially having the property as reported.

"Major proportion" means that a material or monomer is used at greater than 50 wt. %.

"Primary component" means that a material or monomer is the more common substance or has the higher concentration in the mixture or polymer compared to others but may not be as much as 50 wt. %.

The transitional phrase "consisting essentially of" limits the scope of a claim to the specified materials but includes those that do not materially affect the basic and novel characteristics of the claimed materials. These characteristics include open time, cohesive strength (tensile strength), peel strength and viscosity. Meaningful amounts of a third polymer or amounts of a tackifier materially affect the basic and novel characteristics of the claimed materials.

"Hot-melt processable" means that an adhesive composition may be liquefied using a hot-melt tank (i.e., a system in which the composition is heated so that it is substantially in liquid form) and transported via a pump (e.g., a gear pump or positive-displacement pump) from the tank to the point of application proximate a substrate or other material; or to another tank, system, or unit operation (e.g., a separate system, which may include an additional pump or pumps, for delivering the adhesive to the point of application). Hot-melt tanks used to substantially liquefy a hot-melt adhesive typically operate in a range from about 38° C. to about 230° C. Generally, at the point of application, the substantially liquefied adhesive composition will pass through a nozzle or bank of nozzles, but may pass through some other mechanical element such as a slot. A hot-melt processable adhesive composition is to be contrasted with a composition that requires a conventional extruder, and the attendant pressures and temperatures characteristic of an extruder, to liquefy, mix, and/or convey the composition. While a hot-melt tank and pump in a hot-melt processing system can handle adhesive-composition viscosities in a range from about 1000 centipoise to about 10,000 centipoise, an extruder can handle and process adhesive-composition viscosities in a range from about 10,000 centipoise to viscosities of several hundred thousand centipoise.

Unless otherwise noted, "Laminated structure" or "laminate" means a structure in which one layer, material, component, web, or substrate is adhesively bonded, at least in part, to another layer, material, component, web, or substrate. As stated elsewhere in this application, a layer, material, component, web, or substrate may be folded over and adhesively bonded to itself to form a "laminated structure" or "laminate."

FIG. 1 is a plan view of an exemplary, non-limiting embodiment of a diaper 20 of the present invention in a flat, uncontracted state (i.e., without elastic induced contraction). The garment-facing surface 120 of the diaper 20 is facing the viewer. The diaper 20 includes a longitudinal centerline 100 and a lateral centerline 110. The diaper 20 may comprise a chassis 22. The diaper 20 and chassis 22 are shown to have a front waist region 36, a rear waist region 38 opposed to the front waist region 36, and a crotch region 37 located between the front waist region 36 and the rear waist region 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The outer periphery of chassis 22 is defined by longitudinal side edges 12 and end edges 14. The chassis 22 may have opposing longitudinal side edges 12 that are oriented generally parallel to the longitudinal centerline 100. However, for better fit, longitudinal side edges 12 may be curved or angled to produce, for example, an "hourglass" shape diaper when viewed in a plan view. The chassis 22 may have opposing lend edges 14 that are oriented generally parallel to the lateral centerline 110.

The chassis 22 may comprises a liquid permeable topsheet 24 having longitudinal side edges 25, a backsheet 26, and an absorbent core 28 between the topsheet 24 and the backsheet 26. The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In certain embodiments, the chassis 22 comprises the main structure of the diaper 20 with other features may added to form the composite diaper structure. While the topsheet 24, the backsheet 26, and the absorbent core 28 may be assembled in a variety of well-known configurations, preferred diaper configurations are described generally in U.S. Pat. Nos. 3,860,003; 5,151,092; 5,221,274; 5,554,145; 5,569,234; 5,580,411; and 6,004,306.

The topsheet 24 is generally a portion of the diaper 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. A particularly preferred topsheet 24 is available from BBA Fiberweb, Brentwood, TN as supplier code 055SLPV09U.

Any portion of the topsheet 24 may be coated with a lotion as is known in the art. Examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges;

superabsorbent polymers; absorbent gelling materials; or any other known absorbent material or combinations of materials. These materials may be combined to provide a core 28 in the form of one or more layers (individual layers not shown) that may include fluid handling layers such as acquisition layers, distribution layers and storage layers. The absorbent core 28 may comprise a substrate layer, absorbent polymer material, and a fibrous layer of adhesive (not shown). Such absorbent cores 28 may also include layers (not shown) to stabilize other core components. Such layers include a core cover and a dusting layer. A suitable material for such layers is a spunbonded/meltblown/spunbonded nonwoven having a basis weight between about 10 and 15 g/m$^2$ (the meltblown layer comprises <5 g/m$^2$) as is available from Avgol America, Inc. of Knoxville, N.C. For example, Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222. To reduce the overall size and/or thickness of the absorbent core, and thereby improve wearer comfort and reduce the volume of disposable waste created by a soiled insert, it may be desired to construct an absorbent core using the lowest volumes of core materials possible within performance constraints. Toward this end, examples of suitable materials and constructions for a suitable absorbent core are described in, but are not limited to, U.S. applications Ser. Nos. 12/141,122 and 12/141,124; and U.S. Pat. Nos. 8,017,827; and 8,496,637. These generally describe absorbent core constructions that minimize or eliminate the need for and inclusion of airfelt or other forms of cellulose fiber in combination with particles of superabsorbent polymer (hereinafter, "substantially airfelt-free cores"). The adhesives of the present invention may be used within or near the core to immobilize the core, immobilize absorbent material, or to bond the core substrate to the absorbent polymer material, among other uses. The construction of the absorbent core and adhesives used within the core may be such as described in U.S. Pat. Nos. 8,319,005 and 8,187,240, and in U.S. Publication No. 2012/0316530. In some embodiments, the adhesive may be fibrous or be a net-like structure.

The backsheet 26 is generally positioned such that it may be at least a portion of the garment-facing surface 120 of the diaper 20. Backsheet 26 may be designed to prevent the exudates absorbed by and contained within the diaper 20 from soiling articles that may contact the diaper 20, such as bed sheets and undergarments. In certain embodiments, the backsheet 26 is substantially water-impermeable. Suitable backsheet 26 materials include films such as those manufactured by Tredegar Industries Inc. of Terre Haute, IN and sold under the trade names X15306, X10962, and X10964. Other suitable backsheet 26 materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex, under the designation EXXAIRE. Suitable breathable composite materials comprising polymer blends are available from Clopay Corporation, Cincinnati, OH under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer, as illustrated in the cut-away of FIG. 1. The backsheet 26 may comprise an outer cover 26a and an inner layer 26b. The outer cover 26a may have longitudinal side edges 27a and the inner layer 26b may have longitudinal side edges 27b. The outer cover 26a may be made of a soft, non-woven material. The inner layer 26b may be made of a substantially water-impermeable film. The outer cover 26a and an inner layer 26b may be joined together by adhesive or any other suitable material or method. A particularly suitable outer cover 26a is available from Corovin GmbH, Peine, Germany as supplier code A18AH0, and a particularly suitable inner layer 26b is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

The diaper 20 may also include a fastening system 50. When fastened, the fastening system 50 interconnects the front waist region 36 and the rear waist region 38 resulting in a waist circumference that may encircle the wearer during wear of the diaper 20. The fastening system 50 may comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

FIG. 1 depicts a fastening system 50 having an engaging member 52 and a receiving member 54. The engaging member 52 is shown having an engaging surface 53 that may comprise hooks, loops, an adhesive, a cohesive, or other fastening member. The receiving member 54 may have a surface that allows for engagement of the engaging member 52. The receiving member 54 may comprise hooks, loops, an adhesive, a cohesive, or other fastening component that can receive the engaging member 52. Suitable engaging member 52 and receiving member 54 combinations include but are not limited to hooks/loop, hooks/hooks, adhesive/polymeric film; cohesive/ cohesive, adhesive/adhesive; tab/slot; and button/button hole.

The diaper 20 may include barrier cuffs 60 and/or gasketing cuffs 70. Gasketing cuffs 70 may also be referred to as outer leg cuffs, leg bands, side flaps, leg cuffs, or elastic cuffs. Barrier cuffs 60 may also be referred to as second cuffs, inner leg cuffs or "stand-up" elasticized flaps.

The gasketing cuff 70 may be substantially inelastic or may be elastically extensible to dynamically fit at the wearer's leg. The gasketing cuff 70 may be formed by one or more elastic members 72 (such as elastic strands) operatively joined to the topsheet 24, backsheet 26, or any other suitable substrate used in the formation of the diaper 20. Suitable gasketing cuff construction is further described in U.S. Pat. No. 3,860,003

The barrier cuff 60 may have a distal edge 61 and a proximal edge 63 that run substantially parallel to the longitudinal centerline 100. The barrier cuff 60 may span the entire longitudinal length of the diaper 20. The barrier cuff 60 may be formed by a flap 62 and an elastic member 64 (such as elastic strands). The flap 62 may be a continuous extension of any of the existing materials or elements that form the diaper 20. In other embodiments, such as shown in FIG. 1, the barrier cuff 60 may be a discrete element. In such embodiments, the barrier cuff 60 comprising the flap 62 and the elastic member 64 may be formed then joined to the chassis 22 by a bond 65.

The flap 62 may comprise a variety of substrates such as plastic films and woven or nonwoven webs of natural fibers (e.g., wood or cotton fibers), synthetic fibers (e.g., polyester or polypropylene fibers), or a combination of natural and synthetic fibers. In certain embodiments, the flap 62 may comprise a nonwoven web such as spunbond webs, meltblown webs, carded webs, and combinations thereof (e.g., spunbond-meltblown composites and variants). Laminates of the aforementioned substrates may also be used to form the flap 62. A particularly suitable flap may comprise a nonwoven available from BBA Fiberweb, Brentwood, Tenn. as supplier code 30926. A particularly suitable elastic member is available from Invista, Wichita, Kans. as supplier code T262P. Further description of diapers having barrier cuffs and suitable construction of such barrier cuffs may be found in U.S. Pat. Nos. 4,808,178 and 4,909,803. The elastic member 64 generally spans the longitudinal length of the barrier cuff 60. In other embodiments, the elastic member 64 may span at least the longitudinal length of the barrier cuff 60 within the crotch region 37. It is desirable that the elastic member 64 exhibits sufficient elasticity such that the proximal edge 63 of the barrier cuff 60 remains in contact with the wearer during normal wear, thereby enhancing the barrier properties of the barrier cuff 60. The elastic member 64 may be connected to the flap 62 at opposing longitudinal ends. In certain embodiments, the flap 62 may be folded over onto itself so as to encircle the elastic member 64. A bond 67 may be used to secure the folded section of the flap 62.

The barrier cuffs 60 and/or gasketing cuffs 70 may be treated, in full or in part, with a lotion, as described above with regard to topsheets, or may be fully or partially coated with a hydrophobic surface coating as detailed in U.S. application Ser. No. 11/055,743, which was filed Feb. 10, 2005.

The diaper 20 may include front ears 40 and back ears 42. The front and/or back ears 40, 42 may be unitary elements of the diaper 20 (i.e., they are not separately manipulative elements secured to the diaper 20, but rather are formed from and are extensions of one or more of the various layers of the diaper). In certain embodiments, the front and/or back ears 40, 42 may be discrete elements that are joined to the chassis 22, as shown in FIG. 1. Discrete front and/or back ears 40, 42 may be joined to the chassis 22 by any bonding method known in the art such as adhesive bonding, pressure bonding, heat bonding, and the like. In other embodiments, the front and/or back ears 40, 42 may comprise a discrete element joined to the chassis 22 with the chassis 22 having a layer, element, or substrate that extends over the front and/or back ear 40, 42. The front ears 40 and back ears 42 may be extensible, inextensible, elastic, or inelastic. The front ears 40 and back ears 42 may be formed from nonwoven webs, woven webs, knitted fabrics, polymeric and elastomeric films, apertured films, sponges, foams, scrims, and combinations and laminates thereof. In certain embodiments the front ears 40 and back ears 42 may be formed of a nonwoven/elastomeric material laminate or a nonwoven/elastomeric material/nonwoven laminate. A suitable elastic back ear 42 may be a laminate comprising an elastomeric film (such as is available from Tredegar Corp, Richmond, Va., as supplier code X25007) disposed between two nonwoven layers (such as is available from BBA Fiberweb, Brentwood, Tenn. as supplier code FPN332). While the following embodiments are directed to back ear 42 design and construction, these embodiments are equally applicable to front ear 40 design and construction. It should be recognized that any combination of the following embodiments may be used for the back ear 42 and/or the front ear 40.

In alternative embodiments, the diaper 20 may be preformed by the manufacturer to create a pant. A pant may be preformed by any suitable technique including, but not limited to, joining together portions of the article using refastenable and/or non-refastenable bonds (e.g., seam, weld, adhesive, cohesive bond, fastener, etc.). For example, the diaper 20 of FIG. 1 may be manufactured with the fastening system 50 engaged (i.e., the engaging member 52 is joined to the receiving member 54). As an additional example, the diaper 20 of FIG. 1 may be manufactured with the front ears 40 joined to the back ears 42 by way of a bond such as an adhesive bond, a mechanical bond, or some other bonding technique known in the art. Suitable pants are disclosed in U.S. Pat. Nos. 5,246,433; 5,569,234; 6,120,487; 6,120,489; 4,940,464; 5,092,861; 5,897,545; and 5,957,908.

As noted above, a construction adhesive is typically used to join components of an absorbent article as the absorbent article is being assembled. Nonlimiting examples of such joinder using the construction adhesive include but are not limited to:

core cover to dusting layer sealing;
    backsheet 26 to core 28;
    elastic member 64 to nonwoven and/or film to form a barrier cuff 60 or a gasketing cuff 70.
    nonwoven to vapor permeable film to form a backsheet 26;
    barrier cuffs to topsheet 24;
    receiving member 54 to topsheet 24;
    ear 40, 42 to backsheet 26.
    core substrate layer to core absorbent polymer material As will be recognized, many of these uses involve joinder of a nonwoven material to another material. In some instances nonwoven material is joined to another nonwoven. In other instances, a nonwoven may be joined to a film.

Nonwovens in the present invention may be such as those disclosed in U.S. Patent Application Nos. 61/837,286, 8,388, 594, 8,226,625, 8,231,595, and 8,226,626.

Adhesive

The adhesive composition comprises a first amorphous a-olefin copolymer and a second polymer. The amorphous polymer comprises an amorphous or random polymer comprising butene and one or more an alpha olefin monomer such as ethylene, propene, pentene, octene etc. The second polymer comprises an amorphous material that can act as a diluent, viscosity modifier, extender or plasticizer.

The adhesive material comprises a first polymer comprising a polyolefin copolymer comprising a substantially amorphous or randomly polymerized polymer material comprising 1-butene and a second amorphous polymer comprising a compatible amorphous liquid butene polymer such as a polyisobutylene polymer or similar material. The polyisobutylene polymer comprising a substantial proportion (greater than 50 mole % and often greater than 90 mole %) of a isobutylene monomer.

The first amorphous polymer comprises typically butene (e.g.) 1-butene and can be a copolymer or terpolymer that can contain ethylene, propene or a second $C_{4-40}$ olefin polymer. These substantially amorphous low crystallinity polymers have less than 10% and preferably less than 5% crystalline character.

The amorphous polymer is a butene-based copolymer (the minimum amount is at least about 30 or 40 or 50 or 60 wt. % of 1-butene), which may also be referred to as a random butene-a-olefin copolymer. The butene copolymer includes one or more units, i.e., monomer units, derived from propene, one or more comonomer units derived from ethylene or α-olefins including from 4 to about 20 carbon atoms.

The first copolymer comprises about 30 mole %—about 75 mole %, preferably about 40 mole % to about 70 mole %, about 50 mole %—about 65 mole %, of units derived from butene. In addition to butene-derived units, the present copolymer contains from about 70 mole %—about 30 mole % to about 60 mole %—about 40 mole %, of units derived from preferably ethylene, propene or at least one $C_{5\ to\ 10}$ alphaolefin monomer.

In one or more embodiments, the _-olefin comonomer units can also be derived from other monomers such as ethylene, 1-butene, 1-hexane, 4-methyl-1-pentene and/or 1-octene. Exemplary alpha-olefins are selected from the group consisting of ethylene, butene-1, pentene-1,2-methylpentene-1,3methylbutene-1, hexene-1,3-methylpentene-1, 4-methylpentene-1,3,3-dimethylbutene-1, heptene-1, hexene-1, methylhexene-1, dimethylpentene-1, trimethylbutene-1, ethylpentene-1, octene-1, methylpentene-1, dimethylhexene-1, trimethylpentene-1, ethylhexene-1, methylethylpentene-1, diethylbutene-1, propylpentane-1, decene-1, methylnonene-1, nonene-1, dimethyloctene-1, trimethylheptene-1, ethyloctene-1, methylethylbutene-1, diethylhexene-1, dodecene-1, and hexadodecene-1.

In one or more embodiments, amorphous copolymer comprises about 30 mole %—about 75 mole %, preferably about 40 mole % to about 00 mole % of units derived from butene and from about 70 mole %—about 30 mole % to about 60 mole %—about 40 mole %, about 50 mole %—about 65 mole %, of units derived from at least one alpha-olefin monomer selected from ethylene, propene, 1-hexene or 1-octene. Small amounts of α-olefin monomer(s) can be used in the range of about 0.1 to 20 mole %. The amorphous polymer has a weight average molecular weight (Mw) of about 1,000 to about 25,000 or less, preferably about 2,000 to 20,000.

In one or more embodiments, first copolymer comprises about 30 mole %—about 70 mole %, preferably about 40 mole % to about 60 mole % of units derived from butene and from about 70 mole %—about 30 mole % to about 60 mole %—about 40 mole %, of units derived from propene, while small amounts of α-olefin monomer(s) can be used in the range of about 0.1 to 20 mole %.

The amorphous polymer has a weight average molecular weight (Mw) of about 1,000 to about 50,000 or less, preferably about 5 5,000 to 45,000.

The amorphous copolymer has a viscosity of less than 10,000 mPa·s (1 centipoise [cps]=1 mPa·s), for example about 2000 to 8000 mPa·s, when measured by ASTM D3236 at 190° C. Melt Viscosity was determined according to ASTM D-3236, which is also referred to herein as "viscosity" and/or "Brookfield viscosity".

Some examples of amorphous polyolefin include the Rextac polymers made by Huntsman including Rextac E-62, E-65. See, for example Sustic, U.S. Pat. No. 5,723,546 for a description of the polymers and which is expressly incorporated herein. Other useful amorphous polymers are sold as Vestoplast® and Eastoflex® materials.

The adhesive material comprises a second polymer that is compatible with the 1-butene component in the first copolymer. Such compatibility arises from a liquid amorphous material comprising at least one butene monomer (1-butene, cis and trans-2-butene, and isobutylene) isomer. Unlike conventional plasticizing oils such as white oils having a conventional hydrocarbon character, useful materials are sufficiently compatible and as a result improve add-on processability characteristics, reduce viscosity, maintain adhesive bond while improving cohesive properties. The term "compatible or compatibility" of a blend of polymers, as the term is used in this disclosure, means that (1) the materials blend into a uniform hot melt and (2) the cohesive strength of a mixture (70/30 to 50/50) by weight of the amorphous 1-butene polymer and the second amorphous polymer is maintained for construction purposes. Preferred materials comprise a compatible extender, diluent, and viscosity modifier such as a polyisobutylene polymer. The polymer can comprise major proportion of isobutylene units or can be represented as:

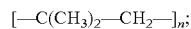

$[-C(CH_3)_2-CH_2-]_n$;

wherein n=15 to 75. Preferred materials such as a polyisobutylene are viscous liquids with molecular weight of about 200-20,000, about 200-5,000 or about 500-3,000. The preferred liquid materials have a Saybolt Universal seconds (SUS) viscosity at 100 °C. of about 100 to 20,000. The characteristic features of polyisobutylene are low gas permeability and high resistance to the action of acids, alkalis, and solutions of salts, as well as high dielectric indexes. They degrade gradually under the action of sunlight and ultraviolet rays (the addition of carbon black slows this process). In industry, polyisobutylene is produced by ionic (AlCl3 catalyzed) polymerization of the monomer at temperatures from −80° to −100° C.; they are processed using the ordinary equipment of the rubber industry. Polyisobutylene combines easily with natural or synthetic rubbers, polyethylene, polyvinyl chloride, and phenol-formaldehyde resins.

In some embodiments, the plasticizers include polypropylene, polybutene, hydrogenated polyisoprene, hydrogenated polybutadiene, polypiperylene, copolymers of piperylene and isoprene, and the like, having average molecular weights between about 350 and about 10,000. In other embodiments, the plasticizers include glyceryl esters of the usual fatty acids.

As noted above, embodiments of preferred compositions are made substantially free of an effective amount of a conventional tackifier material that can add any aspect of open time, substrate wetting or tack to the adhesive material. Avoiding the use of a tackifier reduces costs and frees formulators from the use of materials in short supply. Further, tackifier can impart undesirable odor in disposable articles and can also act as carriers of low molecular weight plasticizers (like process oils that are used in SBC based adhesives) that can weaken the polyethylene back sheet materials used in absorbent articles. Back sheet integrity is becoming more important due to the downsizing of the polyethylene film thickness used in these articles. The term "conventional tackifier resins" means those resins commonly available in the adhesive art and industry that are used in typical hot melt adhesives. Examples of conventional tackifing resins included in this range include an aliphatic hydrocarbon resins, aromatic modified aliphatic hydrocarbon resins, hydrogenated poly-cyclopentadiene resins, poly-cyclopentadiene resins, gum rosins, gum rosin esters, wood rosins, wood rosin esters, tall oil rosins, tall oil rosin esters, poly-terpene, aromatic modified poly-terpene, terpene-phenolic, aromatic modified hydrogenated poly-cyclopentadiene resins, hydrogenated aliphatic resins, hydrogenated aliphatic aromatic resins, hydrogenated terpene and modified terpene and hydrogenated rosin esters. Often in conventional formulations such resins are used in amounts that range from about 5 to about 65 wt. %. often about 20 to 30 wt. %.

In further embodiments, the compositions disclosed herein optionally can comprise an antioxidant or a stabilizer. Any antioxidant known to a person of ordinary skill in the art may be used in the adhesion composition disclosed herein. Non-limiting examples of suitable antioxidants include amine-based antioxidants such as alkyl diphenyl amines, phenyl-naphthylamine, alkyl or aralkyl substituted phenylnaphthylamine, alkylated p-phenylene diamines, tetramethyl-diaminodiphenylamine and the like; and hindered phenol compounds such as 2,6-di-t-butyl-4-methylphenol; 1,3,5-trimethyl-2,4,6-tris(3',5'-di-t-butyl-4'-hydroxybenzyl)benzene; tetra kis[(methylene(3,5-di-t-butyl-4-hydroxyhydrocinnamate)]methane (e.g., IRGANOXTM-1010, from Ciba Geigy, N.Y.); octadecyl-3,5-di-t-butyl-4-hydroxycinnamate (e.g., IRGANOXTM 1076, commercially available from Ciba Geigy) and combinations thereof. Where used, the amount of the antioxidant in the composition can be from about greater than 0 to about 1 wt. %, from about 0.05 to about 0.75 5 wt. %, or from about 0.1 to about 0.5 wt. % of the total weight of the composition.

In further embodiments, the compositions disclosed herein optionally can comprise an UV stabilizer that may prevent or reduce the degradation of the composition by radiation. Any UV stabilizer known to a person of ordinary skill in the art may be used in the adhesion composition disclosed herein. Non-limiting examples of suitable UV stabilizers include benzophenones, benzotriazoles, aryl esters, oxanilides, acrylic esters, formamidine carbon black, hindered amines, nickel quenchers, hindered amines, phenolic antioxidants, metallic salts, zinc compounds and combinations thereof. Where used, the amount of the UV stabilizer in the composition can be from about greater than 0 to about 1 wt. %, from about 0.05 to about 0.75 wt. %, or from about 0.1 to about 0.5 wt. % of the total weight of the composition.

In further embodiments, the compositions disclosed herein optionally can comprise a brightener, colorant or pigment. Any colorant or pigment known to a person of ordinary skill in the art may be used in the adhesion composition disclosed herein. Non-limiting examples of suitable brighteners, colorants or pigments include fluorescent materials and pigments such as triazine-stilbene, coumarin, imidazole, diazole, titanium dioxide and carbon black, phthalocyanine pigments, and other organic pigments such as IRGAZINB, CROMOPHTALB, MONASTRALB, CINQUASIAB, IRGALITEB, ORASOLB, all of which are available from Ciba Specialty Chemicals, Tarrytown, N.Y. Where used, the amount of the brightener, colorant or pigment in the composition can be from about greater than 0 to about 10 wt %, from about 0.01 to about 5 wt %, or from about 0.1 to about 2 wt % of the total weight of the composition.

The compositions disclosed herein may also optionally comprise a fragrance such as a perfume or other odorant. Such fragrances may be retained by a liner or contained in release agents such as microcapsules that may, for example, release fragrance upon removal of a release liner from or compression on the composition.

In further embodiments, the compositions disclosed herein optionally can comprise filler. Any filler known to a person of ordinary skill in the art may be used in the adhesion composition disclosed herein. Non-limiting examples of suitable fillers include sand, talc, dolomite, calcium carbonate, clay, silica, mica, wollastonite, feldspar, aluminum silicate, alumina, hydrated alumina, glass bead, glass microsphere, ceramic microsphere, thermoplastic microsphere, barite, wood flour, and combinations thereof. Where used, the amount of the filler in the composition can be from about greater than 0 to about 60 wt. %, from about 1 to about 50 wt. %, or from about 5 to about 40 wt. %.

TABLE 1

Exemplary Tackifier-Free Adhesive Compositions

| Component | Embodiment | Wt. % | Wt. % | Wt. % |
|---|---|---|---|---|
| Amorphous polymer | REXTAC E63 or E65 or blends (Sustic technology) | 90-10 | 30-85 | 75-40 |
| Second amorphous polymer | Polyisobutylene | 0-50 | 5-45 | 5-40 |
| Additive | Extender/ diluent | 0-30 | 0.1-20 | 0.1-10 |
| Additive | Brightener | 0.001-0.3 | 0.001-0.1 | 0.001-0.05 |
| Additive | Antioxidant/ stabilizer | 0-20 | 1-20 | 1-15 |

The hot melt adhesive compositions have melt rheology and thermal stability suitable for use with conventional hot melt adhesive application equipment. The blended components of the hot melt adhesive compositions have low melt viscosity at the application temperature, thereby facilitating flow of the compositions through a coating apparatus, e.g., coating die or nozzle, without resorting to the inclusion of solvents or extender oil into the composition. Melt viscosities of the hot melt adhesive compositions are between 1500 cP and 3500 cP or about 2000 cP to 3000 cP in mille Pascal-seconds or centipoise (cP) using a Brookfield thermosel RVT viscometer using a rotor number 27 at 176.66° C. (50 rpm, 350° F.). The hot melt adhesive compositions have a softening point (ASTM D 3461-97 Standard Test Method for Mettler Softening Point Method) of about 80° C. to 140° C., in some embodiments about 115° C. to 130° C.

Another aspect are methods of manufacture employing the hot melt adhesive compositions. The method involves application of the molten compositions to a substrate, followed by contact of the adhesive composition with a second substrate within 0.1 second to 5 seconds after application of the adhesive composition to the first substrate, wherein the contacting results in an adhesive bond between the substrates.

The construction adhesive can be applied using a wide variety of known application methods including but not limited to slot extrusion, sprays, including spiral sprays, and beads. Specific examples include but are not limited to: application of the construction adhesive in a spiral spray or slot coating to join a topsheet to an underlying nonwoven layer;

application of the construction adhesive via slot coating to join an acquisition layer or a distribution layer to a core cover;

application of beads of the construction adhesive located between the nonwoven material comprising the cuff and the backsheet;

application of the construction adhesive in a spiral spray or slot coating to join the topsheet to the backsheet so as to seal the longitudinal edges of the absorbent article;

application of the construction adhesive using slot coating to join a landing zone (i.e. a receiving member) to the backsheet;

application of the construction adhesive using slot coating to join the core cover to the dusting layer;

application of the construction adhesive in a spiral spray to join the core to the backsheet.

application of the construction adhesive in a spiral spray to join the nonwoven material comprising the cuff to the nonwoven material comprising the backsheet.

The adhesive may be applied in an amount of about 1 to about 100 or about 4 to about 90 or about 7 to about 70 grams per square meter (g/m²) of resulting bonded material. The material may be applied in an amount of about 0.1 to about 20 or about 0.2 to about 10 or about 0.3 to about 15 grams per square meter (g/m²) of resulting bonded material. The adhesive material can be used at an add-on rate of 0.5 to 2 g/m², 0.6 to 1.7 g/m² or 0.7 to 1.5 g/m², for absorbent articles.

EXAMPLES

A number of hot melt adhesive compositions were prepared by blending first amorphous copolymer, second compatible copolymer and antioxidant under mixing conditions at elevated temperatures to form a fully homogenized melt. Mixing temperatures varied from about 135 to about 200 °C. preferably about 150 to about 175° C. as needed to obtain uniformity. A traditional heated stirred blade (WiseStir®) mixer was used to ensure full homogenization in a heated container into a final adhesive composition.

Examples 1-3

Hot melt adhesive compositions were formulated by melt blending, as described below, wherein specific components and amounts of the components are shown in the following table 2.

TABLE 2

Experimental Preparations

| Component | Ex. 1 (wt. %) | Ex. 2 (wt. %) | Ex. 3 (wt. %) |
|---|---|---|---|
| Rextac E-65 (1-butene copolymer) | 44.5 | 54.5 | |
| Rextac E-63 (1-butene copolymer) | 30 | 20 | |
| Rextac 2830 (1-butene copolymer) | | | 70 |
| Indapol H-1900 Polyisobutylene (MW 2500) | 24.99 | 24.99 | 29.49 |
| Irganox 1010 (stabilizer) | 0.5 | 0.5 | 0.5 |
| Benotex OB (Optical brightener) | 0.01 | 0.01 | 0.01 |
| Brookfield DV-II + pro Viscosity (cP) Rotation 10 rpm Spindle # SC4-27 | | | |
| 250° F. | 31000 | 23825 | 18200 |
| 275° F. | 13650 | 13175 | 10250 |
| 300° F. | 6265 | 6875 | 6050 |
| 325° F. | 4090 | 4460 | 3850 |
| 350° F. | 3245 | 3060 | 2595 |
| Mettler Softening Point (° C.) | 116 | 115 | 91 |
| Density (g/cm³) | 0.87 | 0.87 | 0.87 |

Comparative Example 1

Hot melt adhesive compositions are formulated by melt blending, as described below, wherein specific components and amounts of the components are shown in the following table 3. Comparative examples 1 and 2 each form a non-uniform composition that has insufficient cohesive/adhesive strength to be usefully measured.

| Component | CEx. 1 (wt. %) | CEx. 2 (wt. %) |
|---|---|---|
| APAO | | 75 |
| Rextac E-63 (1-butene copolymer) | 75 | |
| Polyisobutylene | | 25 |
| White Oil | 25 | |
| Irganox 1010 (Stabilizer) | 0 | 0 |
| Benotex OB (Optical brightener) | 0 | 0 |

TABLE 4

Test Results

| Run | Add-on method - Nordsen ® Hot Melt applic. | Add-on (g/m²) over 120 mm width | Temp (° F./° C.) | Gap (mm) | Air Press. (psi/ Pascal) | Web Speed (inch-sec⁻¹/ m-sec⁻¹) | Ex. | Peak Peel (g/in) | Ave. Peel (g/in) | Peel force (N/cm) |
|---|---|---|---|---|---|---|---|---|---|---|
| 1 | Slot/true coat die | 0.75 | 320/160 | | | 2000/50.8 | Ex. 2 | 190 | 93 | 0.37 |
| 2 | Slot/true coat die | 1 | 310/154.4 | | | 2000/50.8 | Ex. 2 | 202 | 110 | 0.43 |
| 3 | Slot/true coat die | 1 | 320/160 | | | 2000/50.8 | Ex. 2 | 217 | 134 | 0.53 |

TABLE 4-continued

Test Results

| Run | Add-on method - Nordsen ® Hot Melt applic. | Add-on (g/m$^2$) over 120 mm width | Temp (° F./° C.) | Gap (mm) | Air Press. (psi/ Pascal) | Web Speed (inch-sec$^{-1}$/ m-sec$^{-1}$) | Ex. | Peak Peel (g/in) | Ave. Peel (g/in) | Peel force (N/cm) |
|---|---|---|---|---|---|---|---|---|---|---|
| 4 | Slot/true coat die | 1 | 330/165.6 | | | 2000/50.8 | Ex. 2 | 212 | 131 | 0.52 |
| 5 | Slot/true coat die | 1 | 315/157.2 | | | 2000/50.8 | Ex. 2 | 205 | 110 | 0.43 |
| 6 | Slot/true coat die | 0.5 | 320/160 | | | 2000/50.8 | Ex. 2 | 111 | 58 | 0.23 |
| 7 | Slot/true coat die | 0.75 | 320/160 | | | 2000/50.8 | Ex. 2 | 161 | 95 | 0.37 |
| 8 | Slot/true coat die | 0.5 | 320/160 | | | 2000/50.8 | Ex. 1 | 126 | 70 | 0.28 |
| 9 | Slot/true coat die | 0.75 | 320/160 | | | 2000/50.8 | Ex. 1 | 181 | 100 | 0.39 |
| 10 | Slot/true coat die | 0.5 | 320/160 | | | 2000/50.8 | Ex. 3 | 117 | 62 | 0.24 |
| 11 | Slot/true coat die | 0.75 | 320/160 | | | 2000/50.8 | Ex. 3 | 152 | 93 | 0.37 |
| 12 | Slot/true coat die | 1 | 320/160 | | | 2000/50.8 | Ex. 3 | 192 | 123 | 0.48 |
| 13 | Signature | 1 | 360/182.2 | 20 | 40/0.276 | 2000/50.8 | Ex. 2 | 154 | 92 | 0.36 |
| 14 | Signature | 1 | 360/182.2 | 20 | 45/0.310 | 2000/50.8 | Ex. 2 | 164 | 96 | 0.38 |
| 15 | Signature | 1 | 360/182.2 | 25 | 45/0.310 | 2000/50.8 | Ex. 2 | 189 | 102 | 0.4 |
| 16 | Signature | 1.25 | 360/182.2 | 25 | 45/0.310 | 2000/50.8 | Ex. 2 | 201 | 123 | 0.48 |
| 17 | Signature | 1.25 | 360/182.2 | 25 | 45/0.310 | 2000/50.8 | Ex. 3 | 187 | 116 | 0.46 |
| 18 | Signature | 1 | 360/182.2 | 25 | 45/0.310 | 2000/50.8 | Ex. 3 | 158 | 88 | 0.35 |
| 19 | Signature | 1 | 360/182.2 | 25 | 45/0.310 | 2000/50.8 | Ex. 1 | 197 | 122 | 0.48 |
| 20 | Signature | 1.25 | 360/182.2 | 25 | 45/0.310 | 2000/50.8 | Ex. 1 | 232 | 138 | 0.54 |

All tests show adhesion and good bonding. The data from runs 2, 3, 4, 5, 9, 12, 15, 16, 17, 19, and 20 show values that all exceeded requirements for a successful construction adhesive for absorbent articles.

These data indicates that the materials will provide excellent construction bonding in disposable absorbent articles. Note viscosity relates to the resistance to flow of the material under certain conditions. This distinctive property determines the flowability, degree of wetting, and penetration of the substrate by the molten polymer. It provides an indication of its processability and utility as a hot melt adhesive material.

Melt viscosity is generally directly related to a polymer molecular weight and is reported in millipascal-second (mP·s) or centipoise (cP) using a Brookfield DV-II+Pro (Rotation 10 rpm—Spindle #SC4-27) at the stated temperature.

Mettler softening point in degrees Centigrade or degrees Fahrenheit is typically measured using ASTM D3104. The amorphous nature of the polyolefin materials results in a melting point, which is not sharp or definite. Rather as the temperature increases, amorphous polymers gradually change from a solid to a soft and then to a liquid material. No clearly defined glass transition or melting temperature is often noted. This temperature testament that generally measures the precise temperature at which a disc of polymer sample, heated at a rate of 2° C. per minute or 10° F. per minute becomes soft enough to allow the test object, a steel ball (grams) drops through the sample. The softening point of a polymer reported in degrees Centigrade or degrees Fahrenheit is important because it typically indicates the polymer's heat resistance, useful application temperatures and solidification points.

Peel test values were obtained by forming a laminate from a SMS non-woven (11.6 g/m$^2$) micro-porous polyethylene film (0.5 mil/0.127 micron) using lamination conditions as shown in Table 4. The laminate is cut into 1 inch/25.4 mm wide strips in the cross machine direction. Peel force was measured by separating the laminate at room temperature using a TMax pull tester at a rate of 20 in/sec (50.8 cm/sec) with the peek force averaged over a 15 period.

The claims may suitably comprise, consist of, or consist essentially of, or be substantially free of any of the disclosed or recited elements. The invention illustratively disclosed herein can also be suitably practiced in the absence of any element which is not specifically disclosed herein.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An absorbent article having a longitudinal centerline and a lateral centerline, a front waist region with a front waist edge, a rear waist region with a rear waist edge, a crotch region disposed between the front waist region and the rear waist region, and two spaced apart longitudinal side edges joining the front waist edge to the rear waist edge, wherein the absorbent article comprises an assembly of components, and wherein the assembly of components comprises:
   a) a topsheet;
   b) a backsheet underlying the topsheet;
   c) an absorbent core disposed between the topsheet and the backsheet, wherein the absorbent core comprises at least one of a core cover, a dusting layer, an acquisition layer, a distribution layer, and a storage member;

d) at least one additional component selected from the group consisting of:
  i) a fastening system for joining the front waist region to the rear waist region when the absorbent article is worn;
  ii) barrier cuffs lying adjacent and inboard the two spaced apart longitudinal side edges;
  iii) gasketing cuffs lying between each of the two spaced apart longitudinal side edges and the barrier cuffs;
  iv) front ears disposed in the front waist region;
  v) back ears disposed in the rear waist region; and
  vi) a receiving member; and e) an adhesive composition joining at least two of the assembly of components together, wherein the adhesive composition comprises at least 90 wt. % of a copolymer, wherein the copolymer comprises from about 30 mole % to about 70 mole % of propene monomer units and from about 30 mole % to about 75 mole % of 1-butene monomer units;

wherein the adhesive composition is free of a heterophase copolymer;

wherein the adhesive composition has a viscosity of less than 10,000 mPa·s at 190° C., as measured by the Viscosity Test Method.

2. The absorbent article of claim 1, wherein the adhesive composition joins the topsheet to an underlying nonwoven layer.

3. The absorbent article of claim 1, wherein the adhesive composition joins the topsheet to the backsheet adjacent one of the two spaced apart longitudinal side edges, wherein the backsheet is substantially water-impermeable.

4. The absorbent article of claim 1, wherein the adhesive composition joins the core cover to the dusting layer.

5. The absorbent article of claim 1, wherein the adhesive composition joins the dusting layer to the backsheet, wherein the backsheet is substantially water-impermeable.

6. The absorbent article of claim 1, wherein the adhesive composition joins the distribution layer to the core cover.

7. The absorbent article of claim 1, wherein the copolymer comprises from about 40 mole % to about 60 mole % 1-butene monomer units.

8. The absorbent article of claim 1, wherein the copolymer has a weight average molecular weight of about 1,000 to about 50,000.

9. The absorbent article of claim 1, wherein the adhesive composition is substantially free of a tackifier.

10. An absorbent article having a longitudinal centerline and a lateral centerline, a front waist region with a front waist edge, a rear waist region with a rear waist edge, a crotch region disposed between the front waist region and the rear waist region, and two spaced apart longitudinal side edges joining the front waist edge to the rear waist edge, wherein the absorbent article comprises an assembly of components, and wherein the assembly of components comprises:
  a) a topsheet;
  b) a backsheet underlying the topsheet;
  c) an absorbent core disposed between the topsheet and the backsheet, wherein the absorbent core comprises at least one of a core cover, a dusting layer, an acquisition layer, a distribution layer, and a storage member;
  d) at least one additional component selected from the group consisting of:
    i) a fastening system for joining the front waist region to the rear waist region when the absorbent article is worn;
    ii) barrier cuffs lying adjacent and inboard the two spaced apart longitudinal side edges;
    iii) gasketing cuffs lying between each of the two spaced apart longitudinal side edges and the barrier cuffs;
    iv) front ears disposed in the front waist region;
    v) back ears disposed in the rear waist region; and
    vi) a receiving member; and
  e) an adhesive composition joining at least two of the assembly of components together, wherein the adhesive composition comprises at least 90 wt. % of a copolymer, wherein the copolymer comprises from about 30 mole % to about 70 mole % of propene monomer units and from about 30 mole % to about 75 mole % of 1-butene monomer units;

wherein the adhesive composition is free of a heterophase copolymer; and wherein the adhesive composition has a density of less than 0.9 g.cm³.

11. The absorbent article of claim 10, wherein the adhesive composition joins the topsheet to an underlying nonwoven layer.

12. The absorbent article of claim 10, wherein the adhesive composition joins the topsheet to the backsheet adjacent one of the two spaced apart longitudinal side edges, wherein the backsheet is substantially water-impermeable.

13. The absorbent article of claim 10, wherein the adhesive composition joins the core cover to the dusting layer.

14. The absorbent article of claim 10, wherein the adhesive composition joins the dusting layer to the backsheet, wherein the backsheet is substantially water-impermeable.

15. The absorbent article of claim 10, wherein the adhesive composition joins the distribution layer to the core cover.

16. The absorbent article of claim 10, wherein the adhesive composition is substantially free of a tackifier.

17. An absorbent article having a longitudinal centerline and a lateral centerline, a front waist region with a front waist edge, a rear waist region with a rear waist edge, a crotch region disposed between the front waist region and the rear waist region, and two spaced apart longitudinal side edges joining the front waist edge to the rear waist edge, wherein the absorbent article comprises an assembly of components, and wherein the assembly of components comprises:
  a) a topsheet;
  b) a backsheet underlying the topsheet;
  c) an absorbent core disposed between the topsheet and the backsheet, wherein the absorbent core comprises at least one of a core cover, a dusting layer, an acquisition layer, a distribution layer, and a storage member;
  d) at least one additional component selected from the group consisting of:
    i) a fastening system for joining the front waist region to the rear waist region when the absorbent article is worn;
    ii) barrier cuffs lying adjacent and inboard the two spaced apart longitudinal side edges;
    iii) gasketing cuffs lying between each of the two spaced apart longitudinal side edges and the barrier cuffs;
    iv) front ears disposed in the front waist region;
    v) back ears disposed in the rear waist region; and
    vi) a receiving member; and e) an adhesive composition joining at least two of the assembly of components together, wherein the adhesive composition comprises at least 90 wt. % of a copolymer, wherein the copolymer comprises from about 30 mole % to about 70 mole % of propene monomer units and from about 30 mole % to about 75 mole % of 1-butene monomer units, and wherein the adhesive composition is substantially free of a tackifier, and wherein the adhesive composition is free of a heterophase copolymer.

18. The absorbent article of claim 17, wherein the adhesive composition has a density of less than 0.9 g.cm$^3$.

19. The absorbent article of claim 17, wherein the adhesive composition joins the topsheet to an underlying nonwoven layer.

20. The absorbent article of claim 17, wherein the adhesive composition is substantially free of a tackifier.

* * * * *